(12) United States Patent
Burch, V et al.

(10) Patent No.: US 11,672,480 B2
(45) Date of Patent: Jun. 13, 2023

(54) WEARABLE FLEXIBLE SENSOR MOTION CAPTURE SYSTEM

(71) Applicants: Reuben F. Burch, V, Columbus, MS (US); Tony Luczak, Starkville, MS (US); David Saucier, Starkville, MS (US); John Ball, Starkville, MS (US); Harish Chander, Starkville, MS (US)

(72) Inventors: Reuben F. Burch, V, Columbus, MS (US); Tony Luczak, Starkville, MS (US); David Saucier, Starkville, MS (US); John Ball, Starkville, MS (US); Harish Chander, Starkville, MS (US)

( * ) Notice: Subject to any disclaimer, the term of this patent is extended or adjusted under 35 U.S.C. 154(b) by 151 days.

(21) Appl. No.: 16/506,932

(22) Filed: Jul. 9, 2019

(65) Prior Publication Data

US 2020/0008745 A1   Jan. 9, 2020

Related U.S. Application Data

(60) Provisional application No. 62/695,602, filed on Jul. 9, 2018.

(51) Int. Cl.
| | | |
|---|---|---|
| *A61B 5/00* | (2006.01) | |
| *A61B 5/0205* | (2006.01) | |
| *A61B 5/024* | (2006.01) | |
| *A61B 5/11* | (2006.01) | |
| *A61B 34/30* | (2016.01) | |

(52) U.S. Cl.
CPC .......... *A61B 5/6804* (2013.01); *A61B 5/0004* (2013.01); *A61B 5/02055* (2013.01); *A61B 5/6807* (2013.01); *A61B 5/7275* (2013.01); *A61B 5/02438* (2013.01); *A61B 5/112* (2013.01); *A61B 5/1121* (2013.01); *A61B 5/1125* (2013.01); *A61B 5/1126* (2013.01); *A61B 5/4504* (2013.01); *A61B 5/4519* (2013.01); *A61B 5/4533* (2013.01); *A61B 34/30* (2016.02); *A61B 2503/10* (2013.01); *A61B 2505/09* (2013.01); *A61B 2560/0214* (2013.01); *A61B 2562/0219* (2013.01); *A61B 2562/164* (2013.01)

(58) Field of Classification Search
CPC .......................... A61B 5/1121; A61B 5/6804
See application file for complete search history.

(56) References Cited

U.S. PATENT DOCUMENTS

| | | |
|---|---|---|
| 8,925,392 B2 | 1/2015 | Esposito |
| 8,961,439 B2 | 2/2015 | Yang |
| 9,427,179 B2 | 8/2016 | Mestrovic |

(Continued)

OTHER PUBLICATIONS

Totaro et al., "Soft Smart Garments for Lower Limb Joint Position Analysis", Oct. 2017, Sensors (Year: 2017).*

(Continued)

*Primary Examiner* — Benjamin S Melhus
(74) *Attorney, Agent, or Firm* — Conley Rose, P.C.

(57) ABSTRACT

The present invention provides a novel system and device for wearables for humans and animals that capture and store kinematic and kinetic data and movement during training, rehabilitation, real-time events, and the like, analyze such data and movement in real-time during and after such activities, and provide output, feedback, assessment, and actionable biomechanical data and information about the wearer.

23 Claims, 8 Drawing Sheets

(56) References Cited

U.S. PATENT DOCUMENTS

| | | | |
|---|---|---|---|
| 10,959,666 B2 | 3/2021 | Yeung | |
| 2003/0163287 A1* | 8/2003 | Vock | G01G 19/44 |
| | | | 702/187 |
| 2012/0253234 A1* | 10/2012 | Yang | A61B 5/1038 |
| | | | 600/595 |
| 2013/0192071 A1* | 8/2013 | Esposito | A43B 17/00 |
| | | | 324/693 |
| 2014/0336538 A1* | 11/2014 | Simonsen | A61B 5/1126 |
| | | | 600/595 |
| 2015/0057967 A1* | 2/2015 | Albinali | A61B 5/1118 |
| | | | 702/150 |
| 2015/0177080 A1* | 6/2015 | Esposito | A61B 5/01 |
| | | | 73/862.01 |
| 2016/0066821 A1* | 3/2016 | Mestrovic | A61B 5/1038 |
| | | | 600/592 |
| 2016/0198995 A1* | 7/2016 | Yeung | A61B 5/1118 |
| | | | 600/595 |
| 2016/0206242 A1* | 7/2016 | Esposito | A61B 5/1038 |
| 2016/0220438 A1* | 8/2016 | Walsh | B25J 9/0006 |
| 2016/0338621 A1* | 11/2016 | Kanchan | A61B 5/6807 |
| 2016/0338644 A1* | 11/2016 | Connor | A61B 5/11 |
| 2017/0036066 A1* | 2/2017 | Chahine | A61B 5/4519 |
| 2017/0172222 A1* | 6/2017 | Morgenthau | H05K 1/165 |
| 2017/0311889 A1* | 11/2017 | Cobanoglu | D03D 1/0088 |
| 2018/0008196 A1* | 1/2018 | Connor | A61B 5/6828 |
| 2018/0020931 A1* | 1/2018 | Shusterman | A61B 5/02116 |
| | | | 600/483 |
| 2018/0093121 A1* | 4/2018 | Matsuura | A63B 21/00185 |
| 2018/0271409 A1* | 9/2018 | Gong | G01B 7/16 |
| 2019/0021634 A1* | 1/2019 | Morris | A61B 5/742 |
| 2019/0046114 A1* | 2/2019 | Bogdanovich | A61B 5/6805 |
| 2019/0132948 A1* | 5/2019 | Longinotti-Buitoni | |
| | | | A61B 5/7278 |
| 2019/0224841 A1* | 7/2019 | Ly | A61B 5/6811 |
| 2019/0234817 A1* | 8/2019 | Sun | G06F 3/0414 |
| 2019/0298987 A1* | 10/2019 | Freeman | A61B 5/282 |
| 2020/0008715 A1* | 1/2020 | Schroeck | A61B 5/1121 |
| 2020/0163621 A1* | 5/2020 | Connor | A61B 5/389 |
| 2020/0281508 A1* | 9/2020 | Ren | A61B 5/4842 |
| 2020/0367823 A1* | 11/2020 | Chahine | A41B 11/00 |
| 2021/0315490 A1* | 10/2021 | Connor | A61B 5/6804 |

OTHER PUBLICATIONS

Burch V, et al., "PFI-RP: From the Ground Up: Using Soft Robotic Sensors to Create a Foot and Ankle Wearable that Accurately Captures Real-time, Kinematic and Kinetic Data During Athletic Training (Abstract)," Aug. 2018, www.nsg.gov/awardsearch/show/Award?AWD_ID=1827652&HistorialAwards, 4 pages.

Luczak, et al., "Closing the wearable gap: Mobile systems for kinematic signal monitoring of the foot and ankle," Electronics, Version Jun. 13, 2018, www.mdpi.com/journal/electronics, pp. 1-22.

* cited by examiner

WEARABLE FLEXIBLE SENSOR MOTION CAPTURE SYSTEM

CROSS-REFERENCE TO RELATED APPLICATION

This application claims priority from U.S. Provisional Patent Application Ser. No. 62/695,602 filed Jul. 9, 2018. The entirety of the provisional application is incorporated herein by reference.

STATEMENT OF GOVERNMENT SUPPORT

This invention was made with government support under grant numbers 1827652 and 1844451 awarded by the National Science Foundation. The government has certain rights in the invention.

FIELD OF THE INVENTION

This invention relates to the field of kinesiology and physical therapy for humans and animals and, more specifically, to a novel system and device or apparatus for wearables or wearable materials for humans and animals that capture and store kinematic and kinetic data and movement during training, rehabilitation, real-time events, and the like, analyze such data, and provide output, feedback, and actionable information to and/or about the wearer.

BACKGROUND OF THE INVENTION

The present invention relates to a new system, device, and microprocessor-based software involving wearable devices for humans and animals that can capture, record, store, and analyze data and physical motion and movement parameter data during exercise, training, real-time events, sporting competitions, rehabilitation, and the like, and provide valuable feedback and information to the subject wearer and/or to medical or training personnel about the wearer. The invention provides a novel wearable flexible sensor motion capture and analysis system for assessing kinematic and kinetic motion and movement of an animal and/or human.

Biomechanical analyses of human joint range of motion (ROM) have evolved from simple goniometric measures to technologically-advanced optical motion capture systems. While motion capture technology aids in the assessment of joint range of motion with gold standard precision measures, the use of this technology is primarily confined within a laboratory setting, with limited applicability to changes in joint angles that occur in everyday tasks.

Traditionally, optical motion capture of biomechanical data collection is considered the gold standard for identifying kinematic and kinetic parameters and is generally confined to a research laboratory or lab-like environment due to the equipment requirements. Unfortunately, high costs and limited access to these research environments reduce the opportunity for improving all athletes, rehabilitation subjects, and the like through technical analysis. One promising technological advancement that has seen increased exposure in research, rehabilitation, and competition is wearable sensor technology and the opportunity to measure near real-time kinematics on the playing field and in subject assessment. Measuring various physiological and kinematic parameters is now accessible to the average athlete and test subject compared to the human and animal activity recognition devices from twenty years ago. Numerous commercially available products utilize micro electromechanical systems (MEMS), accelerometers, and gyroscopes to capture biomechanical measures outside the lab.

One of the benefits of using MEMS devices is that they offer a lower-cost alternative to traditional motion capture solutions. Using an inertial frame, the relative orientation of limb segments can be calculated from accelerometer and gyroscope data. One commonly-used type of MEMS is the inertial measurement unit, or IMU, and this type of sensor is found in most technologies where some form of movement information is captured. However, several recurring issues can be seen in IMU-based motion capture systems including distortion and drift and challenges in how to consistently manage calibration. The distortion and drift that affects actual sensor horizontal and vertical data are due to distortions in non-homogeneous magnetic fields, often caused by building construction materials and magnetic interference. To reduce noise, improved anatomical models and static calibration in defined positions have been developed. However, measurement errors still occur due to skin and segment speed of movement and axial segment rotation. According to Kavanagh et al., the separation of limb segment resultant acceleration could not be identified within the sensor data, resulting in the difficulty to obtain accurate measurements. Additionally, external devices are often incompatible with activities that involve contact and may require frequent adjustment and re-calibration, making them impractical for use in real-world environments.

In human movement, the neuromuscular system senses strains, positioning, and stretching of its proprioceptors and muscular system in order to coordinate limb segment movement. A body network sensor system that mimics strain and stretch around the joints may offer an alternative to using stiff, circuit board-based IMUs in capturing human limb movement. Given calibration and consistency challenges that exist with IMUs used in the athletic wearable market today, a potential solution may lie in the use of a different kind of sensor, or sensors developed for a different purpose, such as soft robotic sensors. Totaro et al. custom designed soft sensors and integrated them into garments for precise movement validated in lower limb joints, but this research does not utilize "off-the-shelf" sensors and therefore are limited for future, real-world environment use cases. Other recent studies utilized more commercialized soft robot sensor solutions found in exoskeletons technologies for less complex movements not located around the foot and ankle. The present invention utilizes sensors, such as soft robotic sensors, that can be identified as silicone-textile (or other soft materials) layered with liquid conductive material and generally identified as resistive, capacitive, or inductive, or a combination thereof. As these sensors are stretched, their resistive, capacitive, or inductive values increase. At the beginning of the research that formed the basis of the invention, two primary soft robotic sensor solutions were available to test. Liquid Wire is a resistance-based sensor produced by Liquid Wire, Inc. and StretchSense™ is a capacitive-based sensor, both of which provide increased output values when stretched past their initial resting lengths. Several advantages for using soft robotic sensors such as these include: (a) the ability to measure biomechanical strain without worry for occlusion errors that typically occur in optical systems and eliminate drift that can occur in MEMS sensors; (b) the realization of small changes in electromechanical specifications during loading and unloading; and (c) the reduction of interference as observed by the wearer. In addition, soft robotic sensors inherently offer "stretchability", which allows the sensors to cover arbitrarily-shaped joints that occur on the human and animal body.

Wearable sensor technology incorporated into socks and other types of clothing exists. For example, U.S. Pat. No. 8,925,392, entitled "Sensors, Interfaces and Sensor Systems for Data Collection and Integrated Remote Monitoring of Conditions at or Near Body Surfaces", discloses a sock that incorporates flexible and stretchable fabric-based pressure sensors. The device may be used for medical purposes like treatment of peripheral neuropathy and it has application in athletics to measure pressure on an athlete's lower extremities.

U.S. Pat. No. 9,427,179 discloses a sock or other garment with pressure sensors for measuring pressure or forces in feet, the stumps of limbs of an amputee fitted with prosthetic devises, or other parts of the body that are subject to pressure-inducing forces.

Products exist that involve sensors in socks that measure a runner's steps, speed, cadence, foot landing, and other measurements. Other patents are directed to wearable sensors that infer joint movement by placing sensors on different limb segments. For example, wearable joint action sensors are described in U.S. patent application Ser. No. 14/963,136. The device of that disclosure measures or detects joint movement by detecting the amount of separation between one limb and a proximity sensor attached to another limb.

Another device is disclosed in U.S. Pat. No. 8,961,439 entitled "System and Method for Analyzing Gait Using Fabric Sensors". That device uses a tension or pressure sensor to sense or quantify a wearer's movement and calculates the wearer's gait by comparing the sensor's measurements with a set of gait parameters.

Due to the intricacy of the ankle complex, for example, precise placement of sensors are required to obtain accurate kinematic data during movement. Ankle complex rotational components can be found within the talocrural, subtalar, and inferior tibofibular joints. Given the anatomical design of the ankle joints, movement of the foot during open kinetic chain in plantar flexion and dorsiflexion do not occur in a single sagittal plane. During plantar flexion, the foot moves 28 degrees in the sagittal plane, one degree in the transverse plane, and four degrees in the frontal plane. Likewise, during dorsiflexion, there are 23 degrees of movement in the sagittal plane, nine degrees in the transverse plane, and two degrees in the frontal plane. Unlike previous research on comparisons of IMUs for optimal motion capture which both ignore internal and external rotations and inversion and eversion, the present invention encompasses the viability of using soft robotic sensors to capture all movement in all three planes.

An important aspect of the invention is the consideration for placement of these sensors in order to optimize measurements of complex ankle and body part movements. Previous work by Mengüci et al. has evaluated the sensor placement at the posterior part of the ankle and heel, extending from the distal aspect of the gastrocnemius muscle complex down to the calcaneous, which has shown positive results in sagittal plane movements (coefficient of determination 0.9680). To capture tri-planar ankle joint movement, one sensor was placed parallel to the distal ⅓ aspect of the fibula, overlaying the lateral malleolus to capture inversion and eversion. A second sensor was placed vertically in-line with the distal ⅓ aspect of the tibia onto the superior aspect of the talus, and a third sensor was positioned perpendicular to the 23-degree axis of inversion. This novel analysis forming the basis of the invention provides a starting point for where sensors should be placed in order to effectively capture full range of ankle, and other joint, motion.

Subject matter experts (SMEs) have identified two additional wearable gaps: (a) there exists a lack of trust and confidence in data output and consistency of motion and movement tracking wearables currently available on the market; and (b) student and professional athletes are often noncompliant and resistant to using wearable technology due to the awkwardness of placement and general discomfort. The present invention addresses these issues and the trust and wearable comfort requirements identified by SMEs via complete transparency into data capture and calculations by publishing algorithms and research results and by integrating the system and apparatus or device of the present invention into existing wearable materials and into uniform requirements, for example.

The present invention and wearable technology provides a distinctive and novel system and device not found in existing technology or products. The invention discloses novel sensor placement and movement measurement. Moreover, soft robotic sensors (SRS), absolute joint angle measurements, use of a puck, i.e., a data acquisition and transmission module, and other features and components of the present invention described herein provide a unique system and device for capturing and assessing accurate kinematic and kinetic motion and movement parameters.

SUMMARY OF THE INVENTION

The present invention provides a new system and apparatus for wearable devices for humans and animals that capture, store, and record kinematic and kinetic data and movement during events in real-time in order to analyze such data and physical movement for exercise, training, sporting competitions, and rehabilitation, while providing valuable output, feedback, and actionable information to the subject wearer and/or to medical or training personnel about the wearer and relevant biomechanical data.

The invention comprises a body part wearable integrating soft robotic sensors (SRSs) into a wearable or compression wearable to capture kinematic and kinetic data of motion or movement during any physical activity, including rigorous training, competition, rehabilitation, athletics, and/or typical task events in real-world environments. Absolute (not inferred) joint angle data can be captured and analyzed in real-time or near real-time using machine learning derived from joint motion modeling and movement and relevant parameter data and through the analysis of data collected in participant motion and movement trials. Output and feedback from the device of the invention provides actionable information to the wearer and/or analyst or trainer about the level of risk associated with ankle or joint movement and placement, the forces applied to the foot and ankle, or other body part, symmetry across both of the wearer's complementary joints or body parts, and additional biomechanical information such as gait, dynamic compound movements (such as jumping), and distance, for example.

SRSs cover a broad range of fabric/cloth/soft materials, for example, that are integrated and embedded with resistive, capacitive, and/or inductive material that is flexible and conductive, providing changes in the electrical properties when stretched or pressure is applied. SRSs utilized in the invention are adapted in a wearable solution capable of accurately capturing kinematic and kinetic data in real-time or near real-time at the individual joint level to provide a meaningful assessment of use, risk of injury, or rehabilitation, for example. Data can be captured and analyzed utilizing machine learning from modeling of body part movements and via the analysis of data collected in participant movement trials. Information from the system and device of the invention provides actionable data, either typically machine readable and/or audible, and may include haptic information or feedback, to the wearer and trainer or tester about relevant body part movement and placement, the force(s) or pressures being applied to the body part, symmetry across the wearer's body part(s), relevant biomechanical information, and the like. The invention captures current, consistent, and accurate data "from the ground up" for making health and safety decisions about a wearer's ankles, toes, knees, elbows, wrists, fingers, and other body parts in need of analysis and functional measurement.

The invention utilizes SRSs to relate sensor stretch with the SRS output, either resistance, capacitance, or inductance, or a combination thereof. SRS sensors were analyzed and found to have linear characteristics, and thus are suitable for linear machine learning movement modeling. The machine learning component of the system can utilize either single or multiple sensor inputs to estimate kinetic and kinematic parameters and does not require the sensor outputs to be linear.

To optimize the design, SRS sensor placement is crucial. Sensor placement studies were performed for ankle complex plantar flexion, dorsiflexion, inversion, and eversion movements.

The plantar flexion SRSs were mounted on the dorsal surface of the foot to measure the downward movement of the foot, such as when the toes are pointed towards the ground and the angle between the dorsal surface of the foot and the lower leg increases. The SRS positions for this movement were determined based on the hallux (big toe) and surface of the top of the foot. The SRS was first oriented towards the hallux, then over the middle of the foot, and lastly towards the 5th phalanx. The SRS oriented towards the hallux was found to be optimal.

The dorsiflexion SRSs were mounted on the heel of the foot to measure the upward movement of the foot towards the lower leg (angle between the top of the foot and lower leg increases). There was only one choice for the dorsiflexion sensor, because the anatomy on the posterior side of the foot, primarily the calcaneus (heel), only provides one location for placement and orientation configuration (POC) to accurately measure dorsiflexion.

The inversion SRSs were mounted on the lateral side of the ankle to measure the movement of the sole (bottom of the foot) towards the midline of the body. These SRS locations were centered around the lateral malleolus (bony landmark on the lateral side of the ankle). The SRSs were first positioned anterior to the lateral malleolus, near to the $5^{th}$ phalanx, then directly over the lateral malleolus, and finally, posterior to the lateral malleolus, close to the heel of the foot. The second position, directly over the lateral malleolus, was selected.

The eversion SRSs were mounted on the medial side of the ankle to measure the movement of the sole away from the midline of the body. The eversion SRSs were determined similarly to the inversion POCs, except they were based on the medial malleolus (bony landmark on the medial of the ankle). The middle position was chosen as best.

Once ankle placement studies had been performed, the system was compared to a state-of-the-art 3D multi-camera motion capture system utilizing MotionMonitor™ (Innovative Sports Training, Inc., Chicago, Ill., USA) software. The MotionMonitor™ system outputs plantar flexion, dorsiflexion, inversion and eversion estimates based on the system tracking multiple body markers using a system of cameras and 3D software. The invention also estimates these outputs, and the invention showed very high linear model fits and very low residuals compared to the motion capture outputs.

With the foregoing and other objects, features, and advantages of the present invention that will become apparent hereinafter, the nature of the invention may be more clearly understood by reference to the following detailed description, preferred embodiments, and appended claims.

BRIEF DESCRIPTION OF THE DRAWINGS

These drawings accompany the detailed description of the invention and are intended to illustrate further the invention and its advantages. The drawings, which are incorporated in and form a portion of the specification, illustrate certain preferred embodiments of the invention and, together with the entire specification, are meant to explain preferred embodiments of the present invention to those skilled in the art. Relevant FIGURES shown or described in the Detailed Description of the Invention are as follows.

DETAILED DESCRIPTION OF THE INVENTION

Figure 1:
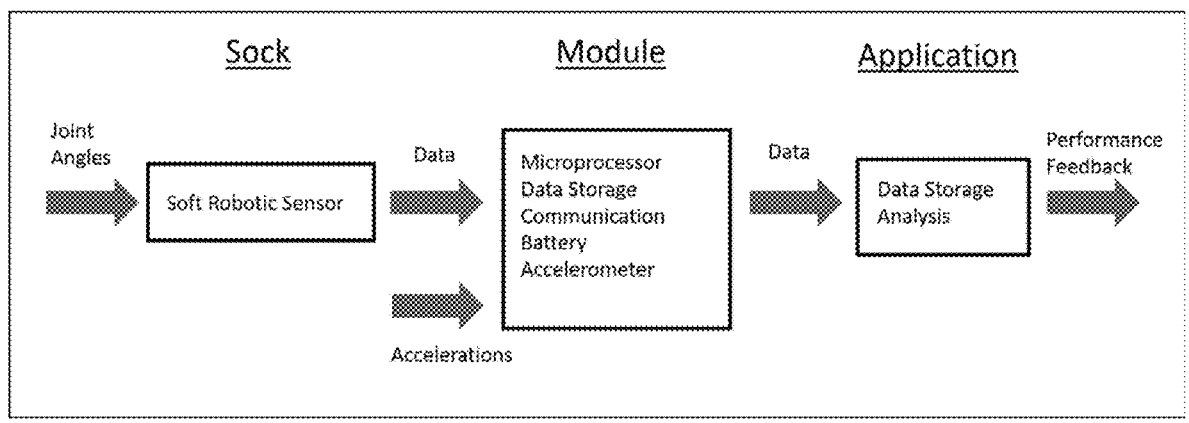
FIG. 1 shows a flow diagram of the different components of the invention.

The present invention provides a novel system and apparatus for wearable devices for humans and/or animals that obtains and records kinematic and kinetic data during real-time events, exercise, training, competition, and rehabilitation, for example, and that analyzes such data and movement and provides feedback, actionable information, and/or assessments to the wearer and/or to medical or training personnel about the wearer, as well as pertinent biomechanical data and assessments. The invention is useable in multiple applications, for both animals and humans, notably concerning sports, any type of training, rehabilitation, and the military, for example.

The present invention consists of a foot-ankle or body part wearable system comprising a wearable apparatus or device integrating one or more sensors, such as SRS sensors, into a wearable or compression garment or sock, for example, to capture kinematic and kinetic data during rigorous or non-rigorous training, testing, and task events in real-world environments. The system and device captures information about selected user joints, muscles, ligaments, bony landmarks, or a combination thereof, senses and monitors motion and movement of the joints, muscles, ligaments, bony landmarks, or a combination thereof of the user, and obtains real-time motion and movement parameter data. The invention further consists of one or more data acquisition and transmission modules, i.e., pucks, for providing power to the sensor and for receiving, transmitting, and storing real time, or near real time, motion and movement parameter data via a wired or wireless protocol for communicating with the sensor. The puck module has the ability to "store-it-forward" and transmit the raw data to a computer or computer-based device where a device app or application analyses and provides feedback based on the raw data. The puck module itself typically will not process the data, but can have the ability to optionally process the motion and movement data. Typically, the puck module at a minimum ensures proper data transmission with the appropriate timestamps. Further, the puck module of the invention has the ability to throttle and/or accelerate the data capture or refresh rate, i.e., the data collection time or rate, of the data from the sensors. Still further, the invention consists of a microprocessor-based data processing means or device for communicating with and receiving and analyzing the motion and movement parameter data from the puck, or data acquisition and transmission module, and for converting such data to motion and movement information and providing such information and characteristics about such motion and movement to the system user or subject being tested and/or an analyst. Such information and characteristics may include the intensity, duration, repetition, and the like, of such motion and movement.

Wearable is defined as an item to be worn or placed on a subject to be tested or analyzed, specifically as a flexible, rigid, or semi-rigid: sock, outerwear, underwear, compression wear, cover, sleeve, harness, band, or garment, or a combination thereof, for example, composed of polymeric or semi-polymeric material, fabric, non-fabric, substrate, a woven, non-woven, and/or knitted material and/or fabric, or a combination thereof. Flexible is defined typically, and as applied to wearables and to the sensors utilized by the invention, as stretchable, variable, bendable, twistable, compressible, pliable, pressable, malleable, and/or tension-able.

Data is or can be captured, saved or stored, and analyzed in real-time or near real-time using machine learning from modeling of the body part, or foot and ankle, movements and through the analysis of data collected in participant movement trials. Output and feedback from the device provides actionable, relevant information and/or assessments to the wearer, evaluator, medical staff, and/or trainer concerning various data parameters including, but not limited to, the level of risk associated with body part, joint, bony landmarks, or ankle movement and placement, the forces applied to the body part, joint, bony landmarks, or foot and ankle, symmetry across both of the wearer's paired joints or ankles, and additional biomechanical information, such as joint kinematics and inferred gait parameters.

FIG. 1 shows a flow diagram of the different components of the invention and shows how joint angle information is translated from movement into data using an SRS via a sock or body part wearable, that such information is stored and transmitted via a data acquisition and transmission module, and that relevant data is converted into human readable performance feedback via an application or microprocessor-based application.

FIGS. 2-8 show visualizations of a proposed prototypical embodiment and design of the invention for a wearable and a puck or data acquisition and transmission module, which in this embodiment attaches to shoelaces of a shoe and provides power to the sensor(s), provides redundant accelerometer readings, and transmits movement data via wired or wireless transmission to a microprocessor-based data processing means. These figures further show the prototypical wearable with preferred components and placements for this particular wearable.

The present invention utilizes key differentiators as compared to the current state of the art. The invention uses sensors such as SRSs to estimate (a) absolute joint angles at the foot and ankle and other relevant assessable bony landmarks, i.e., portions of the body where bones or joints are visually evident, and body parts, and (b) the specific movements of dorsiflexion, plantar flexion, inversion, eversion, abduction, and adduction, for ankles, for example. Current solutions must infer joint angles based on devices placed on limb segments. With inferred angles being the least precise, the use of relative angles can be valuable but have drawbacks based on their lack of consistency. Further, current wearable solutions do not use SRS sensors. SRS sensors are typically fabric-textile or silicone-textile, layered with liquid conductive material and generally identified as resistive, capacitive, or inductive. Advantages of SRS sensors include: (a) the ability to measure biomechanical strain without worry for occlusion errors typical in optical systems and elimination of drift in micro electromechanical device sensors (e.g. Inertial Measurement Units (IMUs)), (b) the realization of small changes in electromechanical readings during loading and unloading, and (c) the reduction of interference as observed by the wearer. In addition, SRS are inherently stretchable, which allows the sensors to cover arbitrarily-shaped human or animal joints. Focusing on SRS for movement capture mitigates issues commonly found in IMU sensors such as distortion and drift, magnetic field disturbance, and calibration challenges. Solutions for other joint wearables have begun to test SRS use, but true capability and functionality of such is unclear.

The invention brings subjects, athletes, rehabilitation specialists, and trainers assessment information about the most injury prone parts of a human and animal body in high levels of training, rehabilitation, and athletic competition. The level of detail typically provided by current products has been limited to a laboratory environment and equipment such as motion capture and force plates. Users, athletes, and trainers may not have frequent access to this level of sophisticated equipment and performing training regimens within a laboratory may not be realistic or practical. Typically, little to no data feedback is available at this level of granularity. The invention brings an extremely precise and efficient level of feedback, particularly concerning absolute joint angle kinematic parameter data, from the laboratory into the actual environment where athletic training, rehabilitation, and real-life activities occur. Further, it allows complete transparency into data capture and calculations via algorithms and integration of the apparatus of the invention into clothing and uniform requirements.

Alternative system and device embodiments and designs include an ankle or joint brace structure, integration into a shoe, sleeve, or harness, or simple elastic straps and/or Velcro-type straps to hold the SRS sensors in place, either directly on the body part or via the wearable. Moreover, alternate embodiments include multiple other specific sensor placement locations and sensors to monitor all six (6) ankle or other joint complex movements and forces or pressures of the foot on the ground, for example. The "puck" of the invention is defined as and is a data acquisition and transmission module that provides power to the SRS sensor or other relevant type of stretch or liquid metal sensor and receives and transmits data values received from the sensors preferably via some form of wireless protocol (e.g., Bluetooth, Wi-Fi, and/or other form of IEEE 802.11 communications protocol or standard, for example) in which communication is provided to a receiving system, such as a mobile computing device. The puck module can accept, transmit, time-stamp, and store data in real-time from any type of robotic sensor type, resistive, capacitive, inductive, or a combination thereof, and can be placed anywhere on the individual being tested, analyzed, or monitored and is not limited to placement on a sock, shoe, and/or the ankle or joint complex region. The sensors can be placed in any number of multiple locations on or around the ankle, joint complex, or bony landmark to capture movement and angles, as well as on the bottom of the foot, within an insole, or in an optimal location near the body part to be analyzed and to record pressure and/or ground or other reaction forces and/or pressures. The invention provides specific optimal placement locations for the sensor(s). Further, such sensors can be integrated into fabrics/textiles/clothing, as depicted in FIGS. 2-8, or they can remain separate and anchored or attached to the ankle, specific joint or body part complex, or bony landmark using, for example, permanent or temporary adhesive materials. Alternatively, certain sensors can be both integrated into a wearable and the same or others attached to relevant body part complexes.

Figure 2:
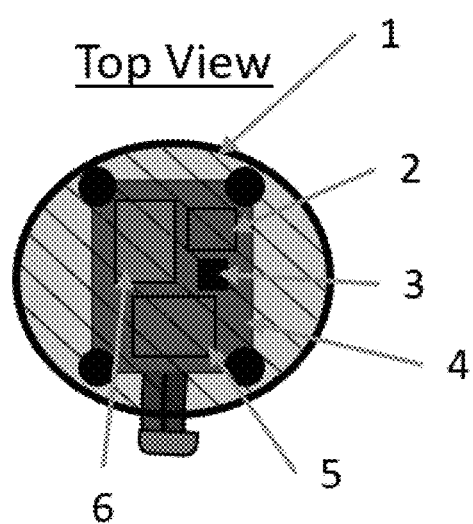
FIG. 2 shows a pictorial representation of the top view of the data acquisition and transmission module of the invention.
Figure 3:
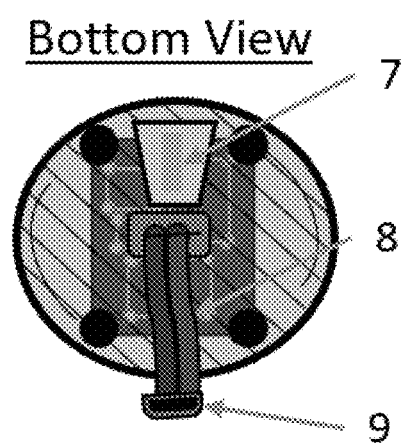
FIG. 3 shows a pictorial representation of the bottom view of the data acquisition and transmission module of the invention.

FIG. 2 shows a top-view visualization of a portion of the invention for one particular body part application and embodiment, specifically a foot-ankle application, and more specifically the puck data acquisition and transmission module 1, which attaches to a user's shoelaces and provides power to the SRS while either sending data to the microprocessor means or performs data computations, via wired or wireless transmission thereto, and redundant accelerometer readings. FIGS. 2-8 show one embodiment of the manner in which the module 1 can be applied to or within clothing or a wearable to connect with sensors in a sock. The module 1 can also be fitted into a pouch on a sock, for example, as well as integration into the insole of a shoe. Attachment to the top of a shoe is but one of many such placement options. The module 1 consists of components housed within a ruggedized casing that covers and protects the module 1, and a bluetooth device 2, or similar communications device, such that the module 1 can connect to and provide communications through wireless protocols such as WiFi, BT, and/or cellular technology, for example, and house multiple antenna types, and whereby the module 1 provides wireless communication to the microprocessor means. Further, the module 1 consists of an accelerometer 3, and/or other Intertial Measurement Unit (IMU) sensors, for example, that provides relevant motion and movement parameter data. Additionally, the module 1 consists of a board 4 that can be a printed circuit board, for example, for mounting the bluetooth 2, accelerometer 3, a lithium battery 5 which provides power to the module 1 and at least one sensor 13 (FIGS. 5, 7, and 8), and an optional module microprocessor or processor 6. FIG. 3 shows a bottom-view visualization of the module 1, specifically at least one shoelace clip 7, for a foot-ankle application, a cable 8 for power, charging, and/or data transmission to/from a sensor, and at least one sock connector 9 for connecting the board 4 to a sensor 13.

Figure 4:
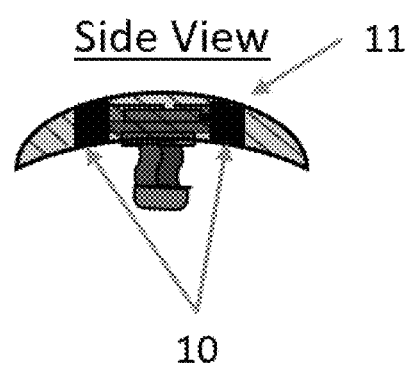
FIG. 4 shows a pictorial representation of the side view of the data acquisition and transmission module of the invention.

FIG. 4 shows a side-view visualization of the module 1, specifically at least one internal rigid support 10 and a curvature 11 to form fit the top of a shoe or the back of the leg or bottom of the foot via an insole, for example.

Figure 5:
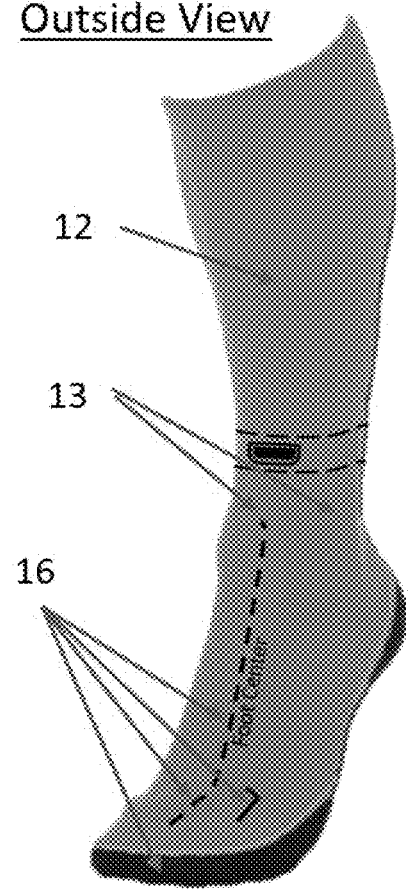
FIG. 5 shows a pictorial representation of the left foot, front outside view of the wearable of the invention.
Figure 6:
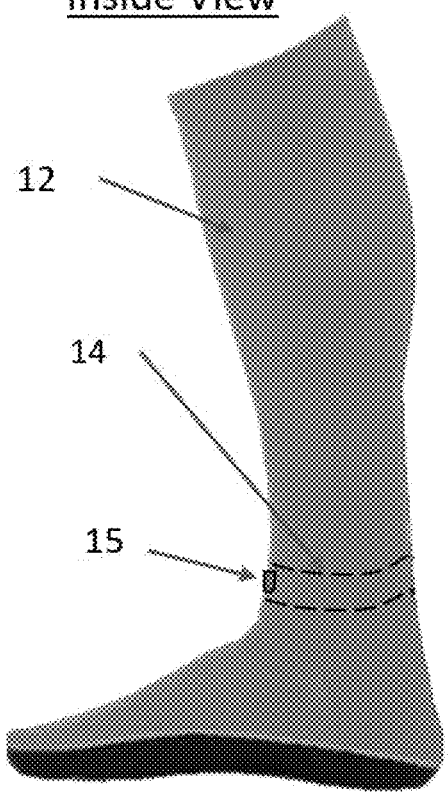
FIG. 6 shows a pictorial representation of the right foot, inside view of the wearable of the invention.

FIG. 5 shows, for an ankle sock embodiment, a left foot, front outside view of the wearable, specifically the wearable compression sock 12, the sensors 13, which can be Liquid Wire sensors, StretchSense sensors, or the like, and visual aids 16 for accurate, proper fit, and placement of the sock or wearable on the body part. FIG. 6 shows a right foot, inside view visualization of the wearable compression sock 12, specifically at least one compression band 14 and a module connector 15 to attach the module 1 and sensor 13 to the sock 12.

Figure 7:
FIG. 7 shows a pictorial representation of the right foot, shoe view of the wearable, sensor, and module of the invention.
Figure 8:
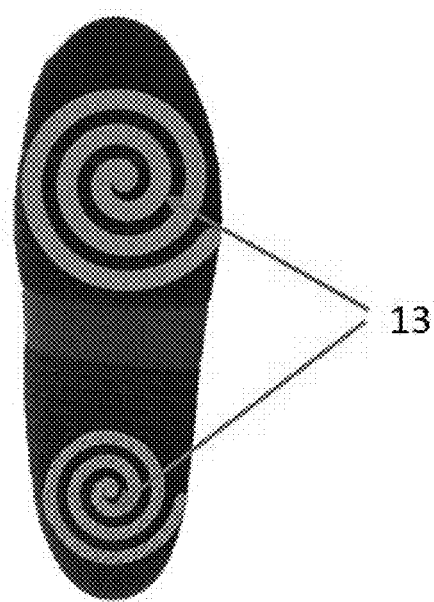
FIG. 8 shows a pictorial representation of the bottom view of the shoe view and sensor and sensor placement of the invention.

FIG. 7 shows a right foot, shoe view visualization of the invention, specifically sensor 13 and module 1. FIG. 8 shows a bottom view visualization of the shoe view, specifically one embodiment of placement of sensors 13. The invention further consists of a body part-specific, or ankle for example, microprocessor-based app or application that provides motion- and movement-specific feedback during and after training or assessment events for the wearer and/or trainer.

The sensors can be Liquid Wire sensors, StretchSense sensors, or any other soft robotic sensor that provides or demonstrates a linear relationship between movement and resistive, capacitive, inductive, or other electronic property output. Machine learning is used to translate sensor output (s) into movement analysis that can be interpreted as specific movements such as plantar flexion, dorsiflexion, inversion, eversion, abduction, and adduction for ankles, for example. The machine learning algorithm is specific to movement dimensions and demographics (e.g., subject individual human or animal height and weight) about a specific individual obtained via the software interface of the invention. A computer-based and/or microprocessor-based system controls the system of the invention. Further, a non-transitory computer-readable medium comprised of computer processor-based and/or microprocessor-based instructions utilize the system of the invention to instruct a computer-based and/or microprocessor-based device to receive relevant data and provide relevant test or analysis subject individual information and assessment.

The invention can capture consistent and accurate data "from the ground up" for making health, training, and safety decisions about a wearers' ankles, joints, body parts, and other locations on the human or animal body where sensors are placed. Sensor placement locations typically include joints, knees, elbows, ligaments, feet, ankles, toes, legs, arms, hips, muscles, fingers, wrists, hands, head, neck, shoulders, any bony landmark, or a combination thereof, that provide or accommodate any animal or human body or body part motion or movement.

Additional information can be captured and learned when the device of the invention is placed on both feet, wrists, or compatible complementary body parts, joints, or bony landmarks. Such information includes insight into specific sensor placement, which is a key ingredient of the present invention, gait, gait assessment, leg asymmetry, and general movement performance, all of which factors are very specific to the individual or subject human or animal wearing the device. The wearable device and apparatus of the system of the invention provides the ability to accurately measure foot-ankle, or other joint, angles, heel and toe, or other body part or bony landmark, forces and pressures, either exerting or receiving, allows combining joint angle and force/pressure measurements into machine learning parameters that estimate injury risk, and allows trainers and analysts to better assess and monitor subjects.

The invention can be used on all joints of the human and/or animal body and is not limited to the ankle complex. For example, a wrist design includes liquid metal sensors integrated into a glove and captures the complex movements of the wrist, as well as force (i.e., grip strength) that occurs between the thumb and/or other multiple fingers. Additionally, motion and movement of finger, hand, wrist, elbow, shoulder, hip, knee, foot, and other similar body parts and bony landmarks to be tested, analyzed, and assessed can be integrated into the scheme of the invention. Other joints of the human and animal body can likewise have motion and movement captured and analyzed using alternative embodiments or variations of the invention, depending on specific sensor placement and machine learning algorithm(s) for specific movement models.

While the invention is applicable to athletics, the capabilities of the invention benefit both athletic and non-athletic individuals and animals including the industrial, military, and sports athlete, as well as any subject in recovery or rehabilitation from an injury or in training to prevent an injury. The invention provides a supplement to or replacement of expensive orthopedic gait assessment equipment, for example, to make assessing and quantifying recovery more accessible, particularly when such movement assessment is otherwise inaccessible. For example, goniometer technology is typically a simple single plane, single dimension measurement process for measuring range of motion around a body joint, while three-dimensional motion capture technology for such measurement is lab-based and expensive. On the other hand, the present invention is highly accurate, efficient, inexpensive, multi-dimensional in scope, and both lab and field useable and compatible.

The invention is comprised of a foot-ankle, or other joint or body part or bony landmark, wearable integrating a stretch-type sensor, such as an SRS, into a wearable device, clothing, or sock or compression sock, or similar clothing material, to capture kinematic and kinetic data during exercise, rigorous training, competition, and/or task events in real-world and/or rehabilitation environments. Relevant motion and movement data is captured, stored, and analyzed in real-time or near real-time using machine learning from modeling of foot and ankle movements, or relevant joint or body part movements, and through analysis of data collected in participant movement trials. Output and feedback from the device of the invention provides actionable information to the wearer and/or trainer about the level of risk associated with foot, ankle, joint, or body part movement and placement, the forces applied to the foot, ankle, joint, and/or body part, symmetry across a wearer's relevant body measurement points, and additional biomechanical information on movement patterns, such as gait, distance, and jumping and dynamic compound movements, absolute joint angle, asymmetry, force, temperature, pressure, pulse rate, joint movement data including flexion, extension, hyperextension, circumduction, supination, pronation, rotation, protraction, retraction, elevation, depression, opposition, plantar flexion, dorsiflexion, inversion, eversion, abduction, and adduction, grip strength, joint strength, or a combination thereof, for example. The invention provides consistent, reliable, and accurate real-time data "from the ground up" for making health and safety decisions about a wearer's relevant joints and other measurable body portion(s) of the human or animal body to be assessed and analyzed. The invention provides training and performance and movement assessment via wearables to capture joint movement and relevant real-time biomechanical parameters for analysis. The invention provides optimized specific sensor number and placement, gait assessment (for ankles and feet) validation against motion capture, jumping, running, and other similar dynamic compound movement assessment, for example, machine learning algorithms specific to ankle and joint complex movements, and sensor anchoring designs and textile integration.

All parameters presented herein including, but not limited to, sizes, dimensions, times, temperatures, pressures, amounts, distances, quantities, ratios, weights, volumes, percentages, and/or similar features and data and the like, for example, represent approximate values and can vary with the possible embodiments described and those not necessarily described but encompassed by the invention. Further, references to 'a' or 'an' concerning any particular item, component, material, or product is defined as at least one and could be more than one.

The above detailed description is presented to enable any person skilled in the art to make and use the invention. Specific details have been revealed to provide a comprehensive understanding of the present invention and are used for explanation of the information provided. These specific details, however, are not required to practice the invention, as is apparent to one skilled in the art. Descriptions of specific applications, analyses, materials, components, dimensions, and calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. This disclosure has described the preferred embodiments of the invention, but it should be understood that the broadest scope of the invention includes such modifications as additional or different methods and materials. Many other advantages of the invention will be apparent to those skilled in the art from the above descriptions and the subsequent claims. Thus, the present invention should not be limited by any of the above-described exemplary embodiments.

The processes, devices, products, apparatus and designs, systems, configurations, methods and/or compositions of the present invention are often best practiced by empirically determining the appropriate values of the operating parameters or by conducting simulations to arrive at best design for a given application. Accordingly, all suitable modifications, combinations, and equivalents should be considered as falling within the spirit and scope of the invention.

What is claimed is:
1. A system for capturing and assessing three-dimensional kinematic and kinetic motion and movement of a wearer, the system comprising:
  a flexible wearable sensor system comprising a flexible wearable and at least one flexible soft robotic sensor (SRS) integrated with the flexible wearable, wherein the flexible SRS is adapted to cover bony and surface landmarks of the wearer, wherein the flexible wearable sensor system is configured to sense and monitor motion and movement of the bony and surface landmarks of the wearer, and obtain real-time motion and movement parameter data, wherein the at least one flexible SRS includes a plantar flexion SRS configured to be mounted on a dorsal surface of a foot and to measure downward movement of the foot, wherein the at least one flexible SRS includes an eversion SRS configured to be mounted on a medial side of an ankle of the foot and to measure movement of a sole of the foot away from a midline of a body of the wearer for data capture in a plurality of planes, wherein the at least one flexible SRS includes a stretch SRS configured to be mounted on a top, a bottom, or a side of the foot to measure, for data capture, ankle angles and steps during gait movements, wherein the at least one flexible SRS includes a pressure SRS configured to be mounted on the bottom of the foot to measure force measurements during gait movements of steps, wherein the at least one flexible SRS includes a flexion or inversion SRS configured to be mounted on the top of the foot, a heel of the foot, or the side of the foot and to measure upward, downward, and lateral movements of the foot, and wherein the at least one flexible SRS includes a pressure SRS configured to be mounted on a bottom of the foot to measure force or pressure measurements during gait movements for data capture of steps;

a data acquisition and transmission module encompassed within a ruggedized casing, the data acquisition and transmission module comprising a printed circuit board, an accelerometer, a power supply, a communication device, and a microprocessor, wherein the data acquisition and transmission module is configured to provide power to the flexible SRS, and to receive the real-time motion and movement parameter data via a wired or wireless protocol with the flexible SRS, wherein the data acquisition and transmission module is further configured to receive absolute joint angle kinematic parameter data from the flexible SRS; and a microprocessor-based data processing device configured to receive and analyze the real-time motion and movement parameter data from the data acquisition and transmission module, and to convert the real-time motion and movement parameter data to motion and movement information, wherein the conversion of the real-time motion and movement parameter data to the motion and movement information includes combining a joint angle from the stretch SRS and force measurements from the pressure SRS into machine learning parameters that estimate injury risk according to machine learning movement modeling.

2. The system of claim 1, wherein the microprocessor-based data processing device is configured to analyze in real-time the real-time motion and movement parameter data, and is configured to provide real-time information of risk levels associated with the motion and movement of the bony and surface landmarks, forces, or pressures applied to body parts of the wearer being sensed, symmetries across the body parts, and kinematics and kinetics of the motion and movement of the bony and surface landmarks.

3. The system of claim 1, wherein the flexible SRS is resistive, capacitive, inductive, or a combination thereof.

4. The system of claim 1, wherein the real-time motion and movement parameter data obtained and analyzed is gait, distance, dynamic compound movements, absolute joint angle, asymmetry, force, joint movement data including flexion, extension, hyperextension, circumduction, supination, pronation, rotation, protraction, retraction, elevation, depression, opposition, plantar flexion, dorsiflexion, inversion, eversion, abduction, and adduction, grip strength, joint strength, or a combination thereof.

5. The system of claim 4, wherein the data acquisition and transmission module is adapted to be positioned either on the wearer or on the flexible wearable, and wherein the flexible SRS is positioned either on the wearer or on the flexible wearable in a position determined by sensor placement studies for assessing a bony and surface landmark movement angle.

6. The system of claim 1, wherein the data acquisition and transmission module is configured to modify a data capture rate or a refresh rate from the flexible SRS.

7. The system of claim 1, wherein the microprocessor-based data processing device is configured to provide machine learning data for joint or body part injury analysis or risk.

8. The system of claim 1, wherein the flexible wearable is a: sock, outerwear, underwear, compression wear, cover, sleeve, harness, band, or garment, or a combination thereof, and wherein the flexible wearable is composed of polymeric or semi-polymeric material a woven material, a non-woven material, or a combination thereof.

9. The system of claim 1, wherein the microprocessor-based data processing device is a portable device, smartphone, or computer.

10. The system of claim 1, wherein the at least one flexible SRS includes an inversion SRS configured to be mounted on a lateral side of the ankle of the foot and to measure movement of a sole of the foot toward the midline of the body, and.

11. The system of claim 1, wherein the at least one flexible SRS includes an additional pressure SRS configured to be mounted on a side of the foot to measure, for data capture, pressure on a side of the foot.

12. A non-transitory computer-readable medium comprising computer processor-based instructions that when executed causes:

a flexible wearable sensor system comprising a plurality of soft robotic sensors (SRS) configured to sense and monitor motion and movement of bony and surface landmarks of a wearer, and obtain real-time motion and movement parameter data, wherein the SRS include an inversion SRS configured to be mounted on a lateral side of an ankle of a foot and to measure movement of a sole of the foot toward a midline of a body, wherein the SRS include a dorsiflexion SRS configured to be mounted on a heel of the foot and to measure upward movement of the foot for data capture in a plurality of planes, wherein at least one flexible SRS includes a stretch SRS configured to be mounted on a top, a bottom, or a side of a foot to measure, for data capture, ankle angles and steps during gait movements, wherein at least one flexible SRS includes a pressure SRS configured to be mounted on the bottom of the foot to measure force measurements during gait movements of steps, a data acquisition and transmission module to receive absolute joint angle kinematic parameter data from the flexible wearable sensor system, wherein the data acquisition and transmission module is encompassed within a ruggedized casing, the data acquisition and transmission module comprising a printed circuit board, an accelerometer, a power supply, a communication device, and a microprocessor, and wherein the data acquisition and transmission module is configured to provide power to the SRS, and to receive and store the real-time motion and movement parameter data obtained from the SRS; and a microprocessor-based data processing device to receive the real-time motion and movement parameter data from the data acquisition and transmission module, and analyze the real-time motion and movement parameter data to determine motion and movement information, wherein the determination of the motion and movement information includes combining a joint angle from the stretch SRS and force measurements from the pressure SRS into machine learning parameters that estimate injury risk according to machine learning movement modeling.

13. The non-transitory computer-readable medium of claim 12, further comprising computer processor-based instructions of a machine learning algorithm, specific to the motion and movement of the bony and surface landmarks of the wearer from modeling of joint angle movement data, to determine risk assessment, treatment, or a combination thereof, concerning the motion and movement of the bony and surface landmarks, and wherein the microprocessor-based data processing device is a portable smartphone.

14. The non-transitory computer-readable medium of claim 12, wherein the SRS include a plantar flexion SRS configured to be mounted on a dorsal surface of the foot and to measure downward movement of the foot, and wherein the SRS include an eversion SRS configured to be mounted on a medial side of the ankle and to measure movement of the sole of the foot away from the midline of the body.

15. A wearable device for capturing and assessing three-dimensional kinematic and kinetic motion and movement of a wearer, the wearable device comprising:
a flexible wearable;
a flexible soft robotic sensor (SRS) integrated with the flexible wearable, the flexible SRS adapted to cover selected bony and surface landmarks of the wearer and configured to sense and monitor motion and movement of the bony and surface landmarks, and to obtain real-time motion and movement parameter data,
wherein the SRS includes a stretch SRS,
wherein the SRS includes flexion or inversion SRS configured to be mounted on a top of a foot, a heel of the foot, or a side of the foot and to measure upward, downward, and lateral movements of the foot for data capture in a plurality of planes, and
wherein the SRS include a pressure SRS configured to be mounted on a bottom of the foot to measure force measurements during gait movements for data capture of steps;
a data acquisition and transmission module encompassed within a ruggedized casing, the data acquisition and transmission module comprising a printed circuit board, an accelerometer, a power supply, a communication device, and a microprocessor,
wherein the data acquisition and transmission module is configured to provide power to the flexible SRS, and to receive the real-time motion and movement parameter data via a wired or wireless protocol with the flexible SRS, and
wherein the data acquisition and transmission module is further configured to receive absolute joint angle kinematic parameter data from the flexible SRS;
and a microprocessor-based data processor configured to receive and analyze the real-time motion and movement parameter data from the data acquisition and transmission module, and to convert the real-time motion and movement parameter data to motion and movement information,
wherein the conversion of the real-time motion and movement parameter data to the motion and movement information includes combining a joint angle from the stretch SRS and force measurements from the pressure SRS into machine learning parameters that estimate injury risk according to machine learning movement modeling.

16. The wearable device of claim 15, wherein the microprocessor-based data processor is configured to analyze in real-time the motion and movement parameter data and is configured to provide real-time information of risk levels associated with the motion and movement of the bony and surface landmarks, forces, or pressures applied to body parts of the wearer being sensed, symmetries across the body parts, and kinematics and kinetics of the motion and movement of the bony and surface landmarks.

17. The wearable device of claim 15, wherein the flexible SRS is resistive, capacitive, inductive, or a combination thereof.

18. The wearable device of claim 15, wherein the motion and movement parameter data obtained and analyzed is gait, dynamic compound movements, distance, absolute joint angle, asymmetry, force, joint movement data including flexion, extension, hyperextension, circumduction, supination, pronation, rotation, protraction, retraction, elevation, depression, opposition, plantar flexion, dorsiflexion, inversion, eversion, abduction, and adduction, grip strength, joint strength, or a combination thereof.

19. The wearable device of claim 18, wherein the data acquisition and transmission module is adapted to be positioned either on the wearer or on the flexible wearable, and wherein the flexible SRS is positioned either on the wearer or on the flexible wearable in a position determined by sensor placement studies for assessing a bony and surface landmark movement angle.

20. The wearable device of claim 15, wherein the data acquisition and transmission module is configured to modify a data capture rate or a refresh rate from the flexible SRS.

21. The wearable device of claim 15, wherein the flexible wearable is a: sock, outerwear, underwear, compression wear, cover, sleeve, harness, band, or garment, or a combination thereof, and wherein the flexible wearable is composed of polymeric or semi-polymeric material, a woven material, a non-woven material, or a combination thereof.

22. The wearable device of claim 15, wherein the stretch SRS is a plantar flexion SRS configured to be mounted on a dorsal surface of the foot and to measure downward movement of the foot.

23. The wearable device of claim 15, wherein the at least one flexible SRS includes an additional pressure SRS configured to be mounted on a side of the foot to measure, for data capture, pressure on a side of the foot.

* * * * *